(12) United States Patent
Kawasaki et al.

(10) Patent No.: US 7,528,081 B2
(45) Date of Patent: May 5, 2009

(54) FABRIC PROTECTANT

(75) Inventors: Maki Kawasaki, Toyonaka (JP);
Tadahiro Matsunaga, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 741 days.

(21) Appl. No.: 10/783,072

(22) Filed: Feb. 20, 2004

(65) Prior Publication Data
US 2005/0186874 A1   Aug. 25, 2005

(51) Int. Cl.
*A01N 53/06* (2006.01)
*A01N 43/32* (2006.01)
*D06M 16/00* (2006.01)
*D06M 23/02* (2006.01)

(52) U.S. Cl. ..................... 442/123; 43/132.1
(58) Field of Classification Search ............... 442/123; 43/132.1
See application file for complete search history.

(56) References Cited

U.S. PATENT DOCUMENTS

| 4,889,872 | A | 12/1989 | Naumann et al. |
| 6,225,495 | B1 | 5/2001 | Ujihara et al. |
| 6,294,576 | B1 | 9/2001 | Mori |
| 2005/0137250 | A1* | 6/2005 | Tsushima .................. 514/452 |

FOREIGN PATENT DOCUMENTS

| EP | 0 387 078 A1 | 9/1990 |
| EP | 0 962 140 A1 | 12/1999 |
| EP | 962140 A1 * | 12/1999 |
| JP | 62 072601 A | 4/1987 |
| JP | 07-149601 A | 6/1995 |
| JP | 07-285805 A | 10/1995 |
| JP | 08-020503 A | 1/1996 |
| JP | 2000355510 A * | 12/2000 |
| JP | 2002320544 A * | 11/2002 |

OTHER PUBLICATIONS

Translation to Aoki et al. (JP 2000355510) (2000).*
Translation to Takagawa et al. (JP 2002320544) (2002).*

* cited by examiner

*Primary Examiner*—Kelechi C Egwim
(74) *Attorney, Agent, or Firm*—Panitch Schwarze Belisario & Nadel LLP

(57) ABSTRACT

A fabric protectant which is an ester compound given by formula (1):

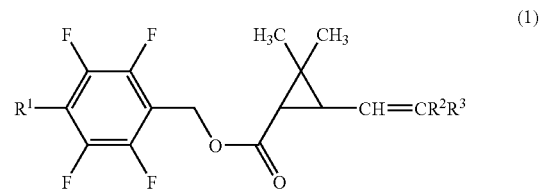

wherein $R^1$ represents a hydrogen atom, methyl group, methoxy group or methoxymethyl group, and $R^2$ and $R^3$ independently represent a chlorine atom, hydrogen atom or methyl group,
and 2,4,6-triisopropyl-1,3,5-trioxane are enveloped in a film selected from the group consisting of polyethylene having 0.91 to 0.94 g/cm³ of density, copolymer of ethylene and vinyl acetate, and copolymer of ethylene and methyl metacrylate is useful for controlling insects which are harmful to fabric and protecting fabric from the insects.

7 Claims, 1 Drawing Sheet

FABRIC PROTECTANT

FIELD OF THE INVENTION

This invention relates to a fabric protectant, which is useful for controlling insects which are harmful to fabric or for protecting the fabric from the insects.

BACKGROUND ART

Hitherto, it is known that various ester compounds of tetrafluorobenzyl alcohol given by formula (1):

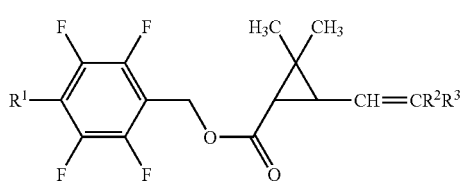

wherein $R^1$ represents a hydrogen atom, methyl group, methoxy group or methoxymethyl group, and $R^2$ and $R^3$ independently represent a chlorine atom, hydrogen atom or methyl group,
are effective for controlling insects which are harmful to fabric in U.S. Pat. Nos. 6,225,495, 6,294,576, 4,889,872 and so on.

In general, fabric protectant is used in the package for preventing damage of fabric by direct contact of the fabric protectant with the fabric. However, the effect of the fabric protectant may decrease by absorption of the active ingredient in the fabric protectant into the envelope.

SUMMARY OF THE INVENTION

The present invention provides a fabric protectant which is an ester compound given by formula (1):

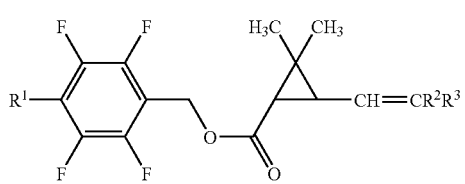

wherein $R^1$ represents a hydrogen atom, methyl group, methoxy group or methoxymethyl group, and $R^2$ and $R^3$ independently represent a chlorine atom, hydrogen atom or methyl group,
and 2,4,6-triisopropyl-1,3,5-trioxane are enveloped in a film selected from the group consisting of polyethylene having 0.91 to 0.94 g/cm³ of density, copolymer of ethylene and vinyl acetate, and copolymer of ethylene and methyl metacrylate.

DISCLOSURE OF THE INVENTION

In the present invention, the ester compound given by formula (1) and 2,4,6-triisopropyl-1,3,5-trioxane are enveloped in a film selected from the group consisting of polyethylene having 0.91 to 0.94 g/cm³ of density, copolymer of ethylene and vinyl acetate, and copolymer of ethylene and methyl metacrylate.

Examples of the ester compound given by formula (1) include 2,3,5,6-tetrafluoro-4-methoxymethylbenzyl 3-(1-propenyl)-2,2-dimethylcyclopropanecarboxylate, 2,3,5,6-tetrafluoro-4-methylbenzyl 3-(1-propenyl)-2,2-dimethylcyclopropanecarboxylate, 2,3,5,6-tetrafluorobenzyl 3-(2,2-dichlorovinyl)-2,2-dimethylcyclopropanecarboxylate, 2,3,5,6-tetrafluoro-4-methoxymethylbenzyl 3-(2-methyl-1-propenyl)-2,2-dimethylcyclopropanecarboxylate, 2,3,5,6-tetrafluoro-4-methoxybenzyl 3-(1-propenyl)-2,2-dimethylcyclopropanecarboxylate and 2,3,5,6-tetrafluoro-4-methoxybenzyl 3-(2-methyl-1-propenyl)-2,2-dimethylcyclopropanecarboxylate. The ester compounds given by formula (1) can be prepared by known methods, for example, the methods described in U.S. Pat. Nos. 6,225,495, 6,294,576 and 4,889,872. The ester compounds have stereoisomers based on the cyclopropane ring and carbon-carbon double bond, and any active isomers and mixtures thereof can be utilized. Further, 2,4,6-triisopropyl-1,3,5-trioxane is a known compound and can be obtained on the market.

In the present invention, the composition enveloped in the film comprises the ester compound given by formula (1) and 2,4,6-triisopropyl-1,3,5-trioxane. The composition may essentially consist of the ester compound given by formula (1) and 2,4,6-triisopropyl-1,3,5-trioxane. In the present invention, the weight ratio of the ester compound given by formula (1) to 2,4,6-triisopropyl-1,3,5-trioxane is usually within the range of 1:8000 to 1:20, preferably 1:4000 to 1:50 by weight. The composition can contain two or more ester compounds given by formula (1). Further, it can contain sublimate fungicide or volatile fungicide such as 3-methyl-4-isopropylphenol, thymol, carvacrol, 4-chloro-3,5-dimethylphenol, 4-chloro-3-methylphenol and hinokitiol.

The composition can be, for example, prepared by mixing the ester compound given by formula (1) and 2,4,6-triisopropyl-1,3,5-trioxane, and optionally the other component, and then pressing to give a tablet. Further, it can be prepared by mixing and melting them under heating, and then putting the melted mixture into a container and cool it to room temperature to form a suitably formed composition. The temperature for melting the mixture is usually within the range of 70 to 200° C.

The composition is enveloped in a film selected from the group consisting of polyethylene having 0.91 to 0.94 g/cm³ of density, copolymer of ethylene and vinyl acetate, and copolymer of ethylene and methyl metacrylate.

The polyethylene having 0.91 to 0.94 g/cm³ of density can be obtained on the market as low density polyethylene (LDPE) or linear low density polyethylene (LLDPE). The copolymer of ethylene and vinyl acetate (EVA) and the copolymer of ethylene and methyl metacrylate (EMMA) are also can be obtained on the market. In general, the thickness of the film is 10 to 100 μm, preferably 20 to 80 μm.

The envelope has generally 0.05 to 50 g, preferably 0.5 to 5 g, of the above-described composition therein. The envelope has usually one composition therein; thus, the weight of the composition is usually 0.05 to 50 g, preferably 0.5 to 5 g.

In the fabric protectant of the present invention, the whole of the above-described composition is usually enveloped in the above-described film. Namely, the fabric protectant can be produced by enveloping the composition in the film entirely or by putting the composition between two sheets of the film and then sealing the edge under heating. However, the fabric protectant of the present invention may have a part of the other material than polyethylene having 0.91 to 0.94 g/cm³ of density, EVA and EMMA in the envelope. The material should be non-permeable to the ester compound given by formula (1). Examples of the material include acrylonitrile-butadiene-styrene (ABS) resin, polyethylene terephthalate (PET) resin, polycarbonate (PC) resin, ethylene-vinyl alcohol copolymer resin and aluminum. The fabric protectant of the present invention can be also obtained by putting the composition in the container made of the material having at least one opening and then covering the opening with polyethylene having 0.91 to 0.94 g/cm$^3$ of density, EVA or EMMA.

The fabric protectant of the present invention is usually kept in a sealed package, wherein the package is made of non-permeable material such as aluminum and the like, and the composition comprising the ester compound given by formula (1) and 2,4,6-triisopropyl-1,3,5-trioxane is not diffused through the package. When the fabric protectant is used, the package is torn and the fabric protectant is taken out to provide for controlling insects which are harmful to fabric and protecting fabric from the insects.

The fabric protectant may be used in various ways; usually, it is placed in the vicinity of fabric and for instance, it may be directly placed in a cabinet drawer, or may be packed in an appropriate container and slung up in a wardrobe. The amount of the ester compound given by formula (1) used for controlling the insects or protecting the fabric is usually 5 to 1500 mg, preferably 50 to 1200 mg per 1 m$^3$ of space. For example, 2.5 to 60 mg of the ester compound given by formula (1) are sufficient to give effect for controlling the insects for 6 months in a 0.05 m$^3$ drawer.

Examples of said fabric to be protected by the fabric protectant of the present invention include clothes, underwear, textile, stockings and gloves. Examples of the material of the fabric include animal fibers such as silk, wool, cashmere and mohair; plant fibers such as cotton and hemp; regenerated fibers such as rayon; semi-synthetic fibers such as acetate fiber and triacetate fiber; and synthetic fibers such as nylon, acryl fiber and polyester fiber.

Examples of the harmful insects include *Attagenus unicolor japonicus* (black carpet beetle), *Authrenus verbasci* (varied carpet beetle), *Dermestes maculates* (hide beetle), *Gibbium aequinoctiale*, *Tinea translucens* (casemaking clothes moth) and *Tineola bisselliella* (webbing clothes moth).

The present fabric protectant generally has a synergistic effect for controlling insects. In addition, it is easy to identify the end point of the fabric protectant as the disappearance of the composition in the envelope is easily observed when the composition essentially consisting of the ester compound given by formula (1) and 2,4,6-triisopropyl-1,3,5-trioxane in the envelope is used.

Further, the effect of the ester compound given by formula (1) and 2,4,6-triisopropyl-1,3,5-trioxane is not decreased by the envelope in the present invention, rather it tends to be increased by enveloped in the above-mentioned film.

Figure 1:
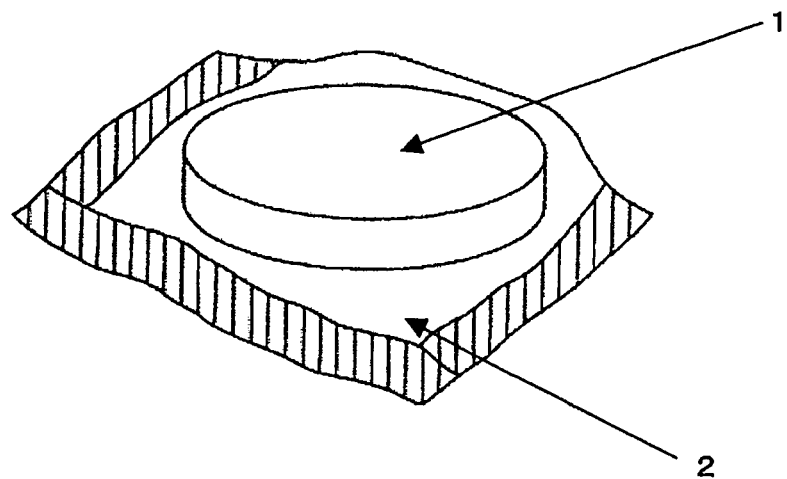
FIG. 1 represents an embodiment of the fabric protectant of the present invention.
Figure 2:
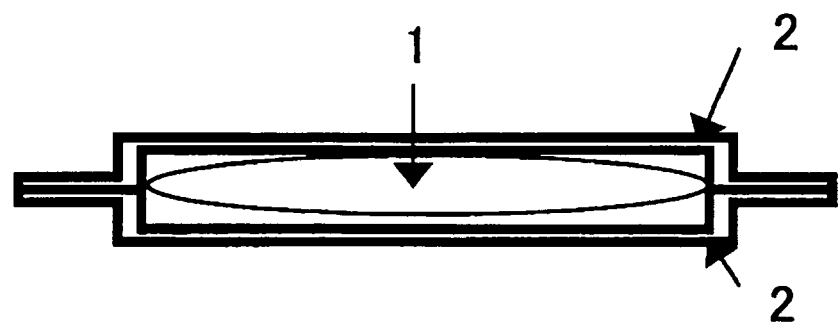
FIG. 2 is a cross section representing an embodiment of the fabric protectant of the present invention.
Figure 3:
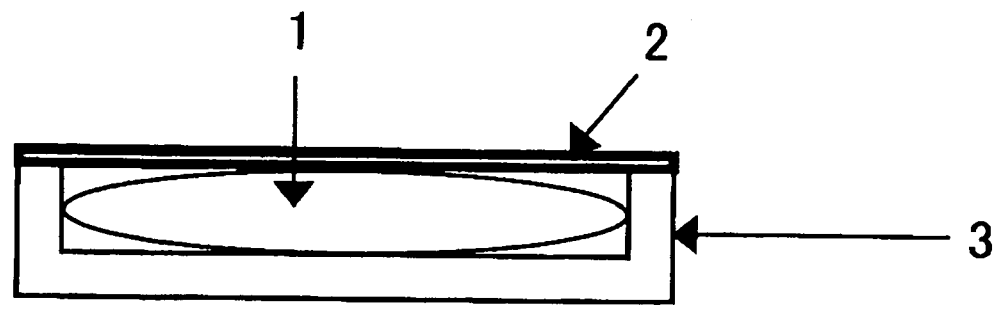
FIG. 3 is a cross section representing an embodiment of the fabric protectant of the present invention, which is in the container of the material non-permeable to the ester compound given by formula (1) and sealed on the opening with a film consisting of polyethylene having 0.91 to 0.94 g/cm$^3$ of density, copolymer of ethylene and vinyl acetate, or copolymer of ethylene and methyl metacrylate.

In the FIGS. 1-3, 1 represents the composition containing the ester compound given by formula (1) and 2,4,6-triisopropyl-1,3,5-trioxane, 2 represents a film of polyethylene having 0.91 to 0.94 g/cm$^3$ of density, copolymer of ethylene and vinyl acetate, or copolymer of ethylene and methyl metacrylate, and 3 represents a container of the material non-permeable to the ester compound given by formula (1).

EXAMPLES

The present invention is explained in more detail by the following examples.

Production Example 1

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness). The tablet was put in linear low density polyethylene film folded in two (5 cm×10 cm, 30 μm in thickness, 0.92 g/cm$^3$ in density, UB-1 produced by Tama-Poly Co.) and sealed on three edges by heating to give a fabric protectant of the present invention. (cf. FIG. 1)

Production Example 2

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness). The tablet was put in EVA film folded in two (5 cm×10 cm, 50 μm in thickness, content of vinyl acetate: 5% by weight, SB-5 produced by Tama-Poly Co.) and sealed on three edges by heating to give a fabric protectant of the present invention. (cf. FIG. 1)

Production Example 3

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness). The tablet was put in EMMA film folded in two (5 cm×10 cm, 40 μm in thickness, content of methyl metacrylate: 5% by weight, WD203-1 produced by Sumitomo Chemical Co.) and sealed on three edges by heating to give a fabric protectant of the present invention. (cf. FIG. 1)

Production Example 4

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness). The tablet was put in low density polyethylene film folded in two (5 cm×10 cm, 30 μm in thickness, 0.925 g/cm$^3$ in density, V-1 produced by Tama-Poly Co.) and sealed on three edges by heating to give a fabric protectant of the present invention.

Production Example 5

The same procedure was carried out as Production Example 1 except that the thickness of the linear low density polyethylene film (UB-1) was 60 μm in place of 30 μm to give a fabric protectant of the present invention.

Production Example 6

The same procedure was carried out as Production Example 4 except that the thickness of the linear low density polyethylene film (V-1) was 60 µm in place of 30 µm to give a fabric protectant of the present invention.

Production Example 7

Two thousand milligrams (2000 mg) of 2,4,6-triisopropyl-1,3,5-trioxane were pressed (4000 kg) to give a disk-shaped tablet (3 cm in diameter and 3 mm in thickness). A hexane solution of 2,3,5,6-tetrafluoro-4-methylbenzyl (1R)-trans-3-(1-propenyl(Z/E=8/1))-2,2-dimethylcyclopropanecarboxylate (ester compound/hexane=1/7.1 by weight) is uniformly painted on the tablet and dried. The tablet was put into the cylindrical container made of copolymer of ethylene-vinyl alcohol (7 cm in diameter, 0.8 cm in height) having an opening on the upper side. The opening is sealed on EMMA film (40 µm in thickness, content of methyl metacrylate: 15% by weight, WH204 produced by Sumitomo Chemical Co.) to give a fabric protectant of the present invention. (cf. FIG. 3)

Production Example 8

Ten milligrams (10 mg) of 2,3,5,6-tetrafluorobenzyl (1R)-trans-3-(2,2-dichlorovinyl)-2,2-dimethylcyclopropanecarboxylate and 2000 mg of 2,4,6-triisopropyl-1,3,5-trioxane are uniformly mixed and pressed (4000 kg) to give a disk-shaped tablet (3 cm in diameter and 3 mm in thickness). The tablet is put in linear low density polyethylene film folded in two (5 cm×10 cm, 30 µm in thickness, 0.92 g/cm$^3$ in density, UB-1 produced by Tama-Poly Co.) and sealed on three edges by heating to give a fabric protectant of the present invention. (cf. FIG. 1)

Production Example 9

Ten milligrams (10 mg) of 2,3,5,6-tetrafluorobenzyl (1R)-trans-3-(2,2-dichlorovinyl)-2,2-dimethylcyclopropanecarboxylate and 2000 mg of 2,4,6-triisopropyl-1,3,5-trioxane are uniformly mixed and pressed (4000 kg) to give a disk-shaped tablet (3 cm in diameter and 3 mm in thickness). The tablet is put in EVA film folded in two (5 cm×10 cm, 50 µm in thickness, content of vinyl acetate: 5% by weight, SB-5 produced by Tama-Poly Co.) and sealed on three edges by heating to give a fabric protectant of the present invention. (cf. FIG. 1)

Production Example 10

Ten milligrams (10 mg) of 2,3,5,6-tetrafluorobenzyl (1R)-trans-3-(2,2-dichlorovinyl)-2,2-dimethylcyclopropanecarboxylate and 2000 mg of 2,4,6-triisopropyl-1,3,5-trioxane are uniformly mixed and pressed (4000 kg) to give a disk-shaped tablet (3 cm in diameter and 3 mm in thickness). The tablet is put in EMMA film folded in two (5 cm×10 cm, 40 µm in thickness, content of methyl metacrylate: 10% by weight, WD201 produced by Sumitomo Chemical Co.) and sealed on three edges by heating to give a fabric protectant of the present invention. (cf. FIG. 1)

Production Example 11

Two thousand milligrams (2000 mg) of 2,4,6-triisopropyl-1,3,5-trioxane are pressed (4000 kg) to give a disk-shaped tablet (3 cm in diameter and 3 mm in thickness). An acetone solution of 2,3,5,6-tetrafluoro-4-methylbenzyl (1R)-trans-3-(1-propenyl(Z/E=8/1))-2,2-dimethylcyclopropanecarboxylate (ester compound/acetone=1/29 by weight) is uniformly painted on the tablet and dried. The tablet is put into the cylindrical container made of copolymer of ethylene-vinyl alcohol (7 cm in diameter, 0.8 cm in height) having an opening on the upper side. The opening is sealed on linear low density polyethylene film (50 µm in thickness, 0.924 g/cm$^3$ in density, F200-0 produced by Sumitomo Chemical Co.) to give a fabric protectant of the present invention. (cf. FIG. 3)

Production Example 12

Two thousand milligrams (2000 mg) of 2,4,6-triisopropyl-1,3,5-trioxane are pressed (4000 kg) to give a disk-shaped tablet (3 cm in diameter and 3 mm in thickness). An acetone solution of 2,3,5,6-tetrafluoro-4-methylbenzyl (1R)-trans-3-(1-propenyl(Z/E=8/1))-2,2-dimethylcyclopropanecarboxylate (ester compound/acetone=1/29 by weight) is uniformly painted on the tablet and dried. The tablet is put into the cylindrical container made of copolymer of ethylene-vinyl alcohol (7 cm in diameter, 0.8 cm in height) having an opening on the upper side. The opening is sealed on EVA film (50 µm in thickness, content of vinyl acetate: 5% by weight, SB-5 produced by Tama-Poly Co.) to give a fabric protectant of the present invention. (cf. FIG. 3)

Production Example 13

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 4000 mg of 2,4,6-triisopropyl-1,3,5-trioxane were uniformly mixed and pressed (4000 kg) to give a disk-shaped tablet (3 cm in diameter and 3 mm in thickness). The tablet was put in linear low density polyethylene film folded in two (5 cm×10 cm, 30 µm in thickness, 0.91 g/cm$^3$ in density and sealed on three edges by heating to give a fabric protectant of the present invention. (cf. FIG. 1)

Production Example 14

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness). The tablet was put in linear low density polyethylene film folded in two (5 cm×10 cm, 30 µm in thickness, 0.91 g/cm$^3$ in density and sealed on three edges by heating to give a fabric protectant of the present invention. (cf. FIG. 1)

Comparative Example 1

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 4000 mg of 2,4,6-triisopropyl-1,3,5-trioxane were uniformly mixed and pressed (4000 kg) to give a disk-shaped tablet (3 cm in diameter and 3 mm in thickness).

Comparative Example 2

Ten milligrams (10 mg) of 2,3,5,6-tetrafluoro-4-methylbenzyl (1R)-trans-3-(1-propenyl(Z/E=8/1))-2,2-dimethylcyclopropanecarboxylate and 2000 mg of 2,4,6-triisopropyl-1,3,5-trioxane were uniformly mixed and pressed (4000 kg) to give a disk-shaped tablet (3 cm in diameter and 3 mm in thickness).

Test Example 1

In a box (725 cm×427 cm×158 cm), two fabric protectants of the present invention were put and kept at 25±2° C. After the designated days, two bags (4.5 cm×4.5 cm) made of cotton cloth (0.2 mm in depth) having 10 to 15 eggs of *Tineola bisselliella* (webbing clothes moth) therein, respectively, were set near the fabric protectants. After one week, the bags were opened and the mortality was observed. The results are given in Table 1.

TABLE 1

| Fabric Protectant | Mortality (%) | |
|---|---|---|
| | After 14 days | After 70 days |
| Production Example 1 | 100 | 100 |
| Production Example 4 | 100 | 100 |
| Production Example 5 | 100 | 96.7 |
| Production Example 6 | 100 | 100 |

Test Example 2

In a box (725 cm×427 cm×158 cm), two fabric protectants of the present invention were put and kept at 25±2° C. After the designated days, two bags (4.5 cm×4.5 cm) made of cotton cloth (0.2 mm in depth) having 10 to 15 eggs of *Tineola bisselliella* (webbing clothes moth) therein, respectively, were set near the fabric protectants. After one week, the bags were opened and the mortality was observed. The results are given in Table 2.

TABLE 2

| Fabric Protectant | Mortality (%) | | |
|---|---|---|---|
| | After 7 days | After 14 days | After 70 days |
| Production Example 2 | 100 | 100 | 100 |

Test Example 3

In a box (725 cm×427 cm×158 cm), two fabric protectants of the present invention were put and kept at 25±2° C. After the designated days, two bags (4.5 cm×4.5 cm) made of cotton cloth (0.2 mm in depth) having 10 to 15 eggs of *Tineola bisselliella* (webbing clothes moth) therein, respectively, were set near the fabric protectants. After one week, the bags were opened and the mortality was observed. The results are given in Table 3.

TABLE 3

| Fabric Protectant | Mortality (%) After 7 days |
|---|---|
| Production Example 3 | 100 |

Test Example 4

In a box (725 cm×427 cm×158 cm), two fabric protectants of the present invention were put and kept at 25±2° C. After the designated days, two bags (4.5 cm×4.5 cm) made of cotton cloth (0.2 mm in depth) having 10 larvae of *Tineola bisselliella* (webbing clothes moth) and cotton cloth (1 cm×1 cm) therein, respectively, were set near the fabric protectants. After one week, the bags were opened and the mortality was observed. The results are given in Table 4.

TABLE 4

| Fabric Protectant | Mortality (%) | |
|---|---|---|
| | After 7 days | After 40 days |
| Production Example 13 | 100 | 100 |
| Production Example 14 | 85 | 100 |
| Comparative Example 1 | 60 | 100 |
| Comparative Example 2 | 65 | 100 |

As shown in Table 4, the fabric protectant of the present invention does not decrease the effect by enveloping, or rather increases the effect at early stage.

What is claimed is:

1. A fabric protection product comprising
   a film selected from the group consisting of polyethylene having 0.91 to 0.94 g/cm³ of density, copolymer of ethylene and vinyl acetate, and copolymer of ethylene and methyl metacrylate, wherein the film envelopes a fabric protection composition comprising,
   an ester compound given by formula (1):

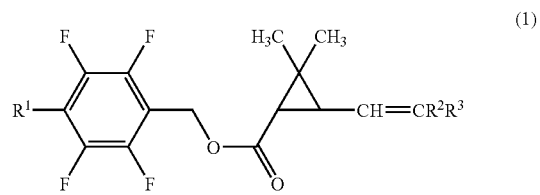

wherein $R^1$ represents a hydrogen atom, methyl group, methoxy group or methoxymethyl group, and $R^2$ and $R^3$ independently represent a chlorine atom, hydrogen atom or methyl group; and
   2,4,6-triisopropyl-1,3,5-trioxane.

2. The fabric protection product according to claim 1, wherein the film is polyethylene having 0.91 to 0.94 g/cm³ of density.

3. The fabric protection product according to claim 1, wherein the film is copolymer of ethylene and vinyl acetate.

4. The fabric protection product according to claim 1, wherein the film is copolymer of ethylene and methyl metacrylate.

5. The fabric protection product according to claim 1, wherein the ester compound is 2,3,5,6-tetrafluoro-4-methoxymethylbenzyl 3-(1-propenyl)-2,2-dimethylcyclopropanecarboxylate, 2,3,5,6-tetrafluoro-4-methylbenzyl 3-(1-propenyl)-2,2-dimethylcyclopropanecarboxylate, 2,3,5,6-tetrafluorobenzyl 3-(2,2-dichiorovinyl)-2,2-dimethylcyclopropanecarboxylate, 2,3,5,6-tetrafluoro-4-methoxymethylbenzyl 3-(2-methyl-1-propenyl)-2,2-dimethylcyclopropanecarboxylate, 2,3,5,6-tetrafluoro-4-methoxybenzyl 3-(1-propenyl)-2,2-dimethylcyclopropanecarboxylate or 2,3,5,6-tetrafluoro-4-methoxybenzyl 3-(2-methyl-1-propenyl)-2,2-dimethylcyclopropanecarboxylate.

6. The fabric protection product according to claim 1, wherein the ester compound is 2,3,5,6-tetrafluoro-4-methylbenzyl 3-(1-propenyl)-2,2-dimethylcyclopropanecarboxylate.

7. The fabric protection product according to claim 1, wherein the ester compound is 2,3,5,6-tetrafluorobenzyl 3-(2,2-dichlorovinyl)-2,2-dimethylcyclopropanecarboxylate.

* * * * *